United States Patent [19]
Gregorovich et al.

[11] Patent Number: 5,945,488
[45] Date of Patent: Aug. 31, 1999

[54] REACTIVE ADDUCTS OF VINYLDIOXO COMPOUNDS

[75] Inventors: Basil Volodymr Gregorovich, Wilmington, Del.; Isidor Hazan, Clementon, N.J.; Hisanori Omura, Clarkston, Mich.

[73] Assignee: E. I. du Pont de Nemours and Company, Wilmington, Del.

[21] Appl. No.: 09/170,339

[22] Filed: Oct. 13, 1998

Related U.S. Application Data

[62] Division of application No. 08/730,861, Oct. 18, 1996, Pat. No. 5,877,332.

[51] Int. Cl.[6] .............................. C08L 19/22; C08L 19/00; C08F 224/00

[52] U.S. Cl. ...................... 525/383; 525/372; 525/375; 525/384; 525/385; 526/266

[58] Field of Search ............................ 526/266; 525/256, 525/372, 375, 383, 385; 549/374

[56] References Cited

U.S. PATENT DOCUMENTS

| | | | |
|---|---|---|---|
| 3,242,144 | 3/1966 | McNally | 260/78.4 |
| 3,245,927 | 4/1966 | Ikeda | 526/266 |
| 3,433,773 | 3/1969 | Kobayashi et al. | 260/78.5 |
| 3,471,430 | 10/1969 | Zimmerman et al. | 260/29.6 |
| 3,849,445 | 11/1974 | Papa et al. | 260/340.9 |
| 3,893,985 | 7/1975 | Papa et al. | 260/80.3 |
| 4,119,617 | 10/1978 | Hanyuda et al. | 528/360 |
| 4,134,884 | 1/1979 | Takiyama et al. | 260/861 |
| 4,157,421 | 6/1979 | Schmidle et al. | 428/419 |
| 4,182,848 | 1/1980 | Schmidle et al. | 528/376 |

OTHER PUBLICATIONS

U.S. application No. 08/186090.
U.S. application No. 08/186367.

*Primary Examiner*—Tae Yoon
*Attorney, Agent, or Firm*—H. L. Fricke

[57] ABSTRACT

New adducts are produced from the reaction of vinyl dioxo compounds with anhydrides, epoxyesters, lactones, and lactams, and such adducts are useful for preparing curable coating compositions.

5 Claims, No Drawings

REACTIVE ADDUCTS OF VINYLDIOXO COMPOUNDS

This is a division of application Ser. No. 08/730,861 filed Oct. 18, 1996, now U.S. Pat. No. 5,877,332.

BACKGROUND OF THE INVENTION

This invention relates to reactive adducts of certain vinyldioxo compounds and to curable coating compositions comprising such reactive adducts.

Vinyldioxo (VDO) compounds are cyclic acetals and are described in detail in U.S. Pat. Nos. 3,010,918; 3,010,923; and 3,197,484 by Ikeda, U.S. Pat. No. 3,014,924 by Brachman, and an article by S. Hochberg entitled *The Chemistry of the Vinyl Cyclic Acetals and Their Air Drying Reactions*, 48 Journal of the Oil and Colour Chemists' Association (JOCCA) 1043–68 (1965). The simplest compounds in this class are made by a reaction of acrolein with a compound having two hydroxyl groups, either on adjacent carbon atoms or on carbon atoms separated by an additional carbon atom. When more than two hydroxyl groups are present in a compound, different pairs of hydroxyl groups can react with the aldehyde to form a cyclic acetal. Typical compounds having at least two hydroxyl groups include, for example, ethylene glycol, glycerin, 1,2,6-hexanetriol, and trimethylolpropane. Depending on the number and type of hydroxyl groups, the resulting VDO can be either a substituted 1,3-dioxolane or a substituted 1,3-dioxane, but frequently it is a mixture of a dioxolane with a dioxane. The reaction of acrolein (1) with trimethylolpropane (2) is shown below in Equation 1. The formation of VDO compounds, like other acetal-forming reactions, is catalyzed by acids.

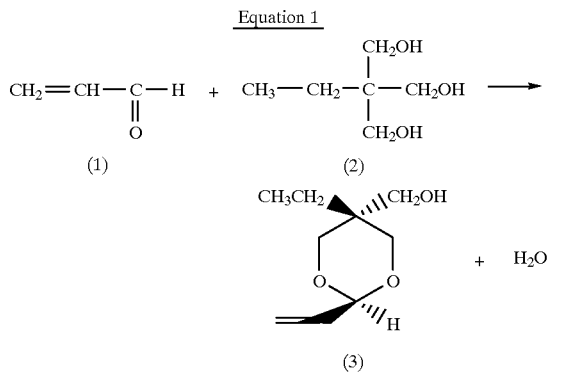

The reaction product according to formula (3) is a 2-vinyl-1,3-dioxane substituted with an ethyl group and a hydroxymethyl (methylol) group in the 5-position. Analogous reactions can be used to prepare substituted rings having four to ten carbon ring members, that is, substituted dioxirane, dioxetane, dioxolane, dioxane, dioxepane, dioxocane, dioxonane, and dioxecane. An improved process for the synthesis of vinyldioxo compounds is disclosed in copending U.S. application Ser. No. 08/435,251, herein incorporated by reference in its entirety.

VDO compounds and their various derivatives have been described as useful polymerizable materials, which have the potential of providing both pigmented and clear-coat finishes in automotive and other applications. Those compounds polymerize in the presence of oxygen, such reactions being catalyzed by cobalt compounds. In an aqueous medium and in the presence of acids, the VDO compounds are unstable, so that further reactions are carried out in either a neutral, alkaline, or organic medium. In spite of the great industrial potential of VDO compounds, they have not been successfully commercialized in high performance coatings.

It has been found that VDO compounds can be polymerized, with ring opening, in the presence of an acid. For example, one of several reactions that take place involves the above compound of formula (3) in the following equation 2:

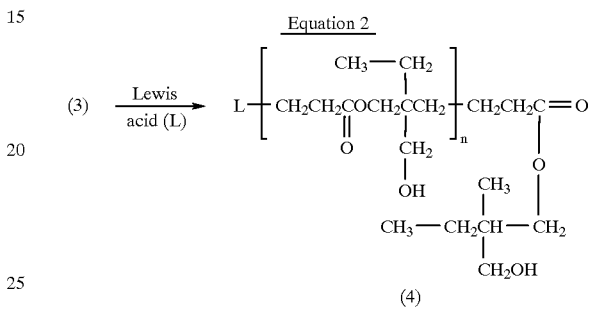

The hydroxyl group attached to the repeating group of the VDO polymer in formula (4) can be used for crosslinking by reaction with a difunctional or polyfunctional compound to form a solid coating. The VDO polymer crosslinking reaction typically comprises one or two liquid components in the absence of a solvent or with a minimum amount of a solvent or diluent.

The copending application designated Ser. No. 08/435,919, herein incorporated by reference in its entirety, discloses a class of adducts formed by reacting VDO compounds with difunctional compounds having two reactive functional groups, at least one of those functional groups being a silyl group, most preferably a di- or trialkoxysilyl group where the alkyl groups have from 1 to 4 carbon atoms, those adducts being represented by the following generic formula (5):

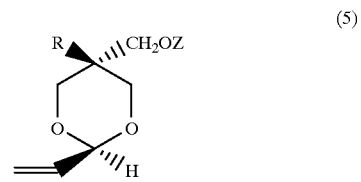

where R is an alkyl having 1 to 12, preferably 1 to 6, carbon atoms, most preferably methyl or ethyl, or R is a branched or cyclic alkyl having 3 to 12, preferably 5 or 6, carbon atoms, and Z is a divalent radical between the oxygen on the VDO moiety and the terminal silyl group.

This invention discloses a class of VDO adducts that display hybrid crosslinkng when used in coating formulations. In particular, VDO compounds as disclosed above are reacted with various cyclic reactants to form VDO adducts. During the formation of the VDO adducts, the cyclic reactants undergo ring opening and the VDO ring structure remains intact. The resultant VDO adducts have two mechanisms by which they can be crosslinked: the VDO ring structure and reactive groups derived from the cyclic compounds that underwent ring opening.

Hybrid crosslinking occurs when the VDO adducts are used in coating formulations in the presence of acid, a traditional crosslinking agent, and optionally an additional catalyst for the crosslinking agent, such that two or more different types of crosslinking reactions occur simultaneously, subsequently, or both. The acid polymerizes the VDO adduct by opening the VDO ring structure. The traditional crosslinking agents react with the reactive groups derived from the cyclic compounds that underwent ring opening. As shown in the examples, the hybrid crosslinking provides superior results when used in coating formulations.

SUMMARY OF THE INVENTION

According to the present invention, there is now provided a class of adducts of a vinyldioxo compounds with a cyclic compounds, the adducts being represented by the formula

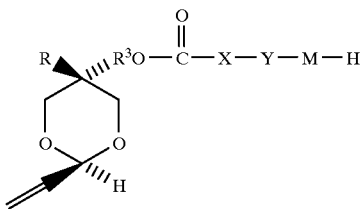

wherein X is selected from the group consisting of linear alkyls having 1 to 12 carbon atoms, branched alkyls having 3 to 12 carbon atoms, and cyclic alkyls having 3 to 12 carbon atoms; Y is selected from the group consisting of $CH_2$, CHR', CR'R", and carbonyls; M is selected from the group consisting of oxygen and nitrogen; and each R, R', R", and $R^3$ is independently selected from the group consisting of linear alkyls having 1 to 12 carbon atoms, branched alkyls having 3 to 12 carbon atoms, and cyclic alkyls having 3 to 12 carbon atoms.

Preferred VDO adducts of this invention include anhydride adducts, epoxyester adducts, lactone adducts, and lactam adducts. Also disclosed are new curable coating compositions comprising such adducts of vinyldioxo compounds.

DETAILED DESCRIPTION OF THE INVENTION

New adducts of vinyldioxo compounds are disclosed herein, and these adducts have been found to have superior results when used in coating compositions. These adducts can readily be formed using a starting VDO compound made from, for example, a vinyl aldehyde and a tri-hydroxyl compound. One such preferred VDO is 2-vinyl-5-ethyl-5-hydroxymethyl-1,3-dioxane made by reacting acrolein and trimethylolpropane as disclosed above. Another preferred VDO is 3,9-divinyl-2,4,8,10-tetraoxaspiro[5.5]undecane, also known as diallylidene pentaerythritol and 3,9-divinylspirobi(m-dioxane), made by reacting acrolein and pentaerythritol. Other VDO compounds useful for this invention include 2-vinyl-5-hydroxy-1,3-dioxane, 2-vinyl-4-hydroxymethyl-1,3-dioxolane, and 2-vinyl-4-(4-hydroxybutyl)-1,3-dioxolane.

These VDO compounds are reacted with various cyclic compounds to form VDO adducts. During the formation of the VDO adducts, the cyclic compounds undergo ring opening and the VDO ring structure remains intact. Equation 3 illustrates the reaction of a generic VDO represented by formula 6 with a generic cyclic compound represented by formula 7 to yield the generic VDO compound of this invention represented by formula 8.

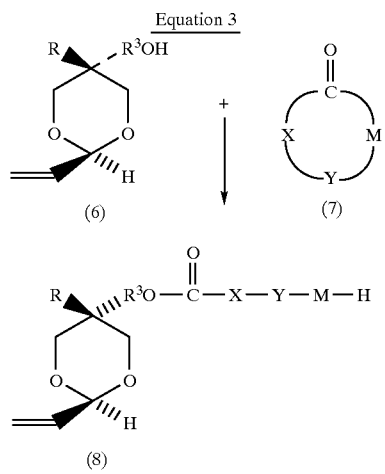

wherein X is selected from the group consisting of linear alkyls having 1 to 12 carbon atoms, branched alkyls having 3 to 12 carbon atoms, and cyclic alkyls having 3 to 12 carbon atoms; Y is selected from the group consisting of $CH_2$, CHR', CR'R", and carbonyls; M is selected from the group consisting of oxygen and nitrogen; and each R, R', R", and $R^3$ is independently selected from the group consisting of linear alkyls having 1 to 12 carbon atoms, branched alkyls having 3 to 12 carbon atoms, and cyclic alkyls having 3 to 12 carbon atoms.

Preferred VDO adducts of this invention include anhydride adducts, epoxyester adducts, lactone adducts, and lactam adducts.

As shown in Equation 4, anhydride adducts represented by formula (9) are formed by reacting VDO represented by formula (6) with a cyclic anhydride represented by formula (10a).

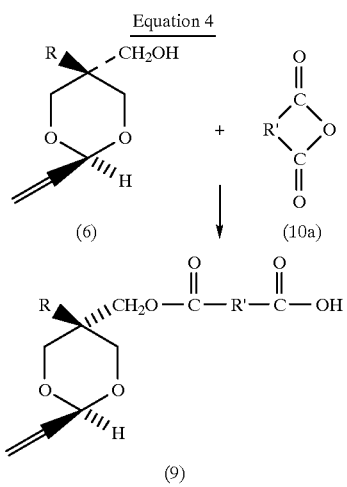

wherein each R and R' is independently selected from the group consisting of linear alkyls having 1 to 12 carbon atoms, preferably 2 to 6 carbon atoms; branched alkyls having 3 to 12 carbon atoms; and cyclic alkyls having 3 to 12 carbon atoms and R' can additionally be phenyl. Preferred cyclic anhydrides useful in this invention include succinic, maleic, hexahydrophthalic, and methyhexahydrophthalic anhydrides.

In a preferred embodiment, Equation 5 shows the reaction of 2-vinyl-1,3-dioxane shown as formula (3) with hexahydrophthalic anhydride shown as formula (10).

Equation 5

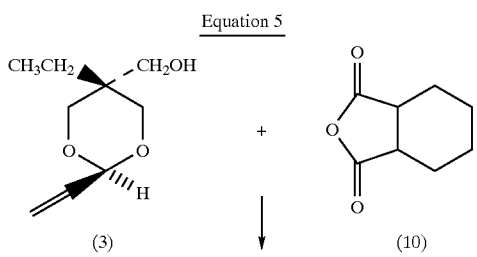

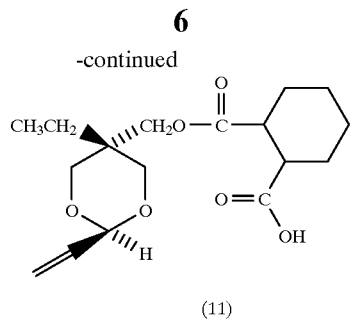

(11)

The anhydride adduct shown in formula (11) has an acid, i.e. carboxyl, reactive group that is derived from opening the anhydride ring of the hexahydrophthalic anhydride. Anhydride adducts are useful in coating compositions that crosslink via reaction of the acid group with epoxy groups such as aliphatic diepoxide. Examples 3 & 4 illustrate anhydride adducts of this invention.

The anhydride adducts can be further reacted with an epoxyester to yield an epoxyester adduct. As shown in Equation 6, the epoxyester represented by formula (12a) reacts with the acid reactive group of the anhydride adduct represented by formula (9) to yield an epoxyester adduct represented by formulas (13a) and (14a), each of which has a hydroxyl reactive group.

Equation 6

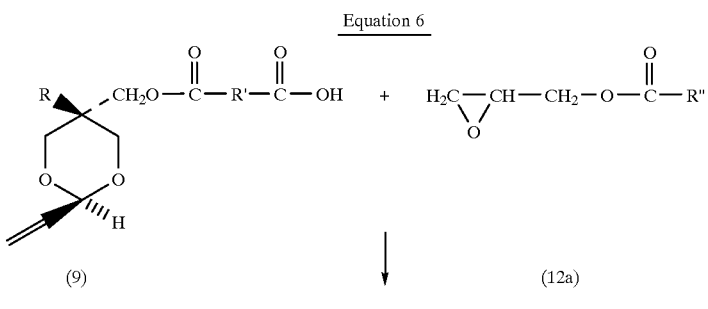

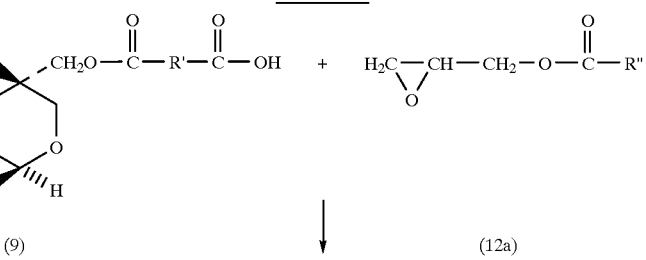

(13a)

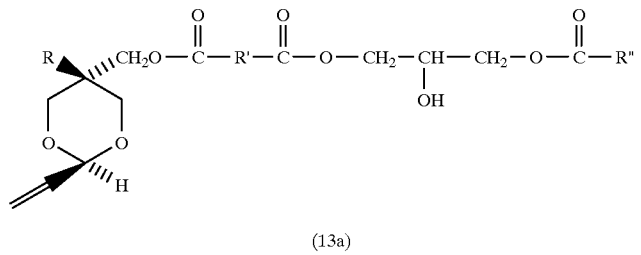

(14a)

wherein each R, R', and R" is independently selected from the group consisting of linear alkyls having 1 to 12 carbon atoms, preferably 2 to 6 carbon atoms; branched alkyls having 3 to 12 carbon atoms; and cyclic alkyls having 3 to 12 carbon atoms and R' can additionally be phenyl. Preferred epoxyesters useful for this invention include glycidyl ester of neodecanoic acid known by the trademark Cardura E10; versatic acid glycidylesters known by the trademark Cardura E911; and pivalic acid glycidylester known by the trademark Cardura E5, all manufactured by Shell Chemical Company.

In a preferred embodiment shown in Equation 7, the anhydride adduct designated as formula (11) is reacted with the epoxyester known as Cardura E10 and represented by formula (12).

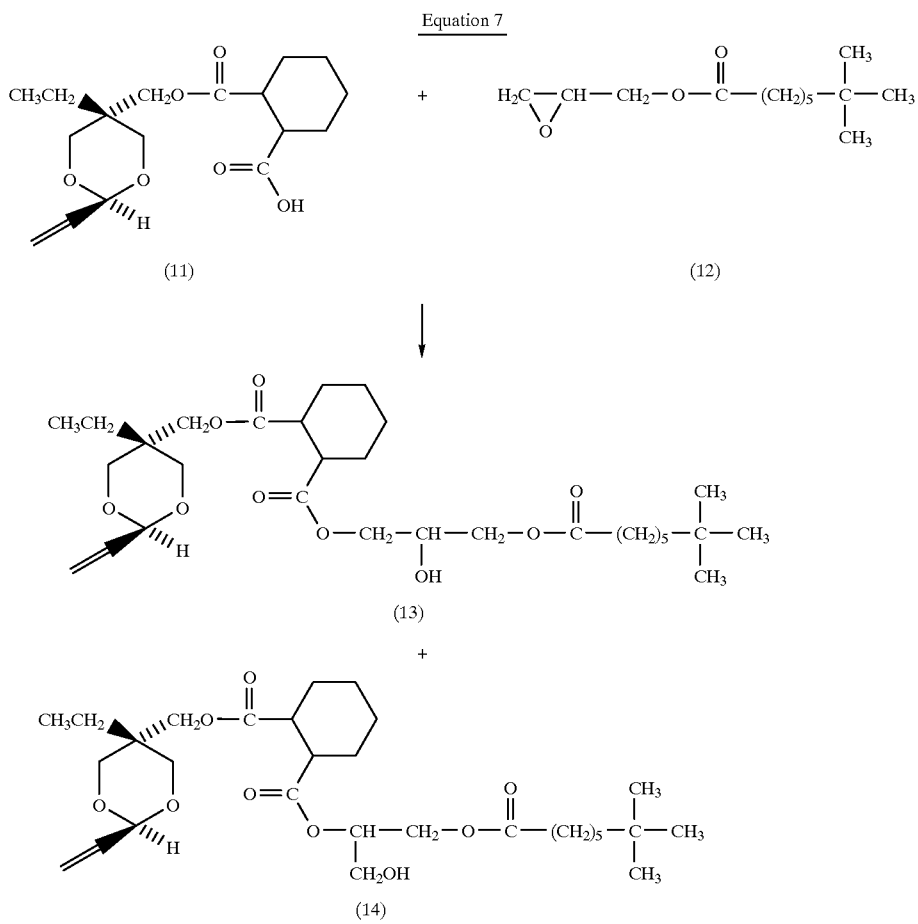

The epoxyester adducts according to formulas (13a), (13), (14a), and (14) all have a hydroxyl reactive group and comprise the VDO ring structure, the open cyclic anhydride structure, and the flexible epoxyester structure. Coating compositions containing epoxyester adducts crosslink via reaction of the hydroxyl group with polyisocyanates, melamine resins, or silanes. Example 5 illustrates an epoxyester adduct of this invention.

As shown in Equation 8, lactone adducts represented by formula (16a) are formed by reacting VDO represented by formula (6) with a cyclic lactone represented by formula (15a).

Equation 8

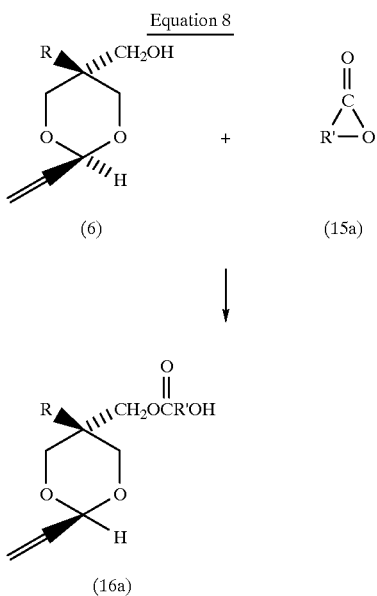

wherein each R and R' is independently selected from the group consisting of linear alkyls having 1 to 12 carbon atoms, preferably 2 to 6 carbon atoms; branched alkyls having 3 to 12 carbon atoms; and cyclic alkyls having 3 to 12 carbon atoms and R' can additionally be phenyl. Preferred cyclic lactones include butyrolactone, caprolactone, valerolactone, and laurolactone.

In a preferred embodiment shown in Equation 9, 2-vinyl-1,3-dioxane represented by formula (3) is reacted with caprolactone represented by formula (15).

Equation 9

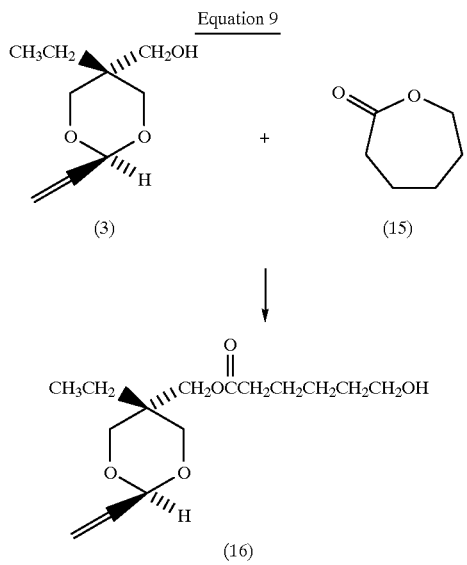

The lactone adduct according to formula (16) contains a hydroxyl reactive group. Lactone adducts are useful in coating compositions that crosslink via reaction of the hydroxyl group with polyisocyanates, melamine resins, or silanes. Example 1 illustrates a caprolactone adduct of this invention, and Example 2 illustrates a clearcoat comprising the caprolactone adduct of Example 1.

As shown in Equation 10, lactam adducts represented by formula (18) are formed by reacting VDO represented by formula (6) with a cyclic lactam represented by formula (17).

Equation 10

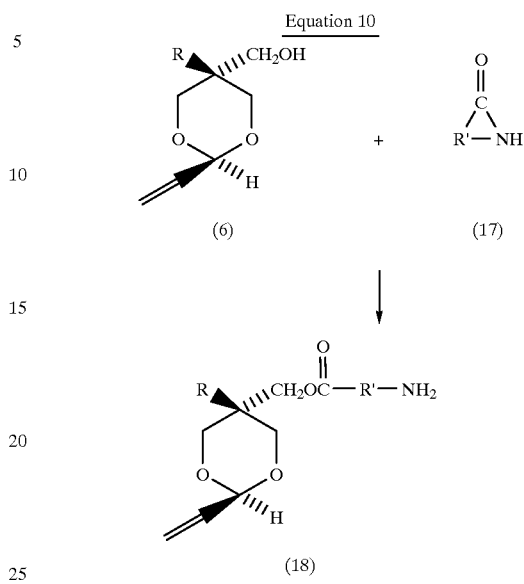

wherein each R and R' is independently selected from the group consisting of linear alkyls having 1 to 12 carbon atoms, preferably 2 to 6 carbon atoms; branched alkyls having 3 to 12 carbon atoms; and cyclic alkyls having 3 to 12 carbon atoms and R' can additionally be phenyl.

Preferred cyclic lactams include butyrolactam, caprolactam, valerolactam, and laurolactam. The lactam adduct according to formula (18) contains an amine reactive group. Lactam adducts are useful in coating compositions that crosslink via reaction of the amine group with polyisocyanates or epoxies.

The anhydride, monoepoxyester, lactone, and lactam adducts described above are useful as coating compositions. The adducts of this invention can be polymerized with an acid catalyst to form coating compositions, wherein the VDO ring structure is opened and the coatings polymerize by a non-oxidative ionic mechanism when the coatings are baked. The coating compositions comprising VDO adducts of this invention can also be added to conventional crosslinkable coating compositions to provide higher solids content than would otherwise be possible, wherein the VDO ring structure remains intact and crosslinking occurs via the reactive groups derived from the cyclic compounds that underwent ring opening.

In a preferred embodiment, the adducts are combined with an acid catalyst and traditional crosslinking agents to yield hybrid crosslinking in the coating, wherein crosslinking occurs by both opening the VDO ring structure and reaction with the reactive groups derived from the cyclic compounds that underwent ring opening. The preferred acid catalyst is a Lewis acid, and traditional crosslinking agents include isocyanates, expoxies, melamine resins, and silanes. An additional crosslinking catalyst may be required depending upon the particular crosslinking agent selected. Superior coatings are produced in part due to the polymerization via opening of the VDO ring structure, which does not produce a byproduct. The reduction in byproducts is advantageous as it reduces volatile organic compound (VOC) emissions and provides a smooth coating by minimizing bubbles and problems associated therewith.

As stated previously, anhydride adducts are useful in coating compositions that crosslink via reaction of the carboxyl group with epoxy groups such as aliphatic diepoxide; epoxyester and lactone adducts are useful coating compositions that crosslink via reaction of the hydroxyl group with polyisocyanates, melamine resins, or silanes; and lactam adducts are useful in coating compositions that crosslink via reaction of the amine group with polyisocyanates or epoxies.

Coating compositions generally comprise a carrier liquid, a film forming polymer, a crosslinking (curing) agent, pigments, and various additives such as U.V. stabilizers, dispersion agents, thickeners, emulsions, anti-oxidants, leveling agents, extenders, etc. For waterborne coatings, the carrier liquid is primarily water, and the carrier liquid is primarily solvent for solventborne coatings. The combination of the film forming polymer and the crosslinking agent is commonly referred to as a binder. Crosslinked polymer microparticles, such as microgels and non-aqueous dispersions (NADs), may be added to the binder to provide the rheology control needed to make low viscosity coatings useful for automotive applications. The term "weight percent solids" means the percentage composition based upon the weight of the coating materials excluding the carrier liquid.

The coating composition can comprise from about 25–95 weight percent solids of the binder, which further comprises from about 10–45 weight percent of a VDO adduct or mixture of VDO adducts of this invention and about 15–40 weight percent of other film forming polymers such as NADs. The coating composition further comprises about 10–40 weight percent of a crosslinking agents or mixture of crosslinking agents, about 0–60 weight percent of a pigment or mixture of pigments, and about 0–15 weight percent of other additives.

Preferably, clearcoat coatings comprise about 40 weight percent solids of the VDO adduct, about 20 weight percent solids of other film forming polymers, about 30 weight percent solids of a crosslinking agent or mixture of crosslinking agents, and about 10 weight percent solids of other additives.

The coating compositions comprising VDO adducts of this invention typically contain a volatile organic compounds (VOC) content in the range of about 0.0–2.8 lb/gal, typically about 1.0–2.8 lb/gal, and the coating compositions can be used as either basecoats or clearcoats. Unlike waterborne or powder coatings, which require special application equipment, the coating compositions comprising VDO adducts of this invention can be applied with the ordinary spray equipment now being used in automobile plants.

This invention is now illustrated by the following representative example. All parts and percentages are by weight unless otherwise indicated.

EXAMPLE 1

This example illustrates the preparation of a caprolactone adduct from the reaction of 2-vinyl-5-ethyl-5-hydroxymethyl-1,3-dioxane (VDO-6) and caprolactone. A reactor was charged with 1751.59 g of VDO-6 and 7 g of tin(II) octoate catalyst, and the reactor was purged with nitrogen. After the reactor contents were heated to 90° C., the caprolactone was drip fed over a period of 2 hours. The reactor contents were held at 90° C. for another two hours, and subsequently allowed to cool.

EXAMPLE 2

This example illustrates a clearcoat coating composition comprising a caprolactone adduct according to Example 1, prepared by blending together the following components:

| Component | Wt. % Solids | Parts by Weight |
| --- | --- | --- |
| Acrylic silane resin | 81.00 | 41.53 |
| NAD (non-aqueous dispersed resin) | 65.50 | 30.53 |
| Silane resin | 100.00 | 10.00 |
| Caprolactone adduct | 100.00 | 10.00 |
| Microgel rheology control agent | 70.00 | 5.71 |
| Silica rheology control dispersion | 34.20 | 7.75 |
| Resiflo ™ polybutyl acrylate flow agent | 50.00 | 0.40 |
| UV screeners (blend) | 97.43 | 4.11 |
| tetramethyl orthoformate | 0.00 | 4.00 |
| DDBSA* | 44.99 | 2.67 |
| Acrylic | 82.80 | 7.13 |
| methylated butylated malamine formaldehyde resin | 95.60 | 8.69 |
| Dibutyl tin dilaurate | 100.00 | 0.10 |

*Dodecyl benzene sulfonic acid, unblocked or blocked with AMP (aminomethylpropyl).

The final clearcoat composition had a weight solids content of 75.40, a measured VOC of 2.7 lbs/gal, and a calculated VOC of 2.12 lbs/gal. Application of the final clearcoat over a solvent borne basecoat yielded a 20° gloss meter reading of 94 and a distinctness of image (DOI) meter reading of 93.

EXAMPLE 3

This example illustrates the preparation of an anhydride adduct from the reaction of 2-vinyl-5-ethyl-5-hydroxymethyl-1,3-dioxane (VDO-6) and methylhexahydrophthalic anhydride (MHHPA). A reactor was charged with 12.29 g of VDO-6 and 11.71 g of MHHPA. After an infrared spectra of the reactor contents were taken, the reactor was placed in a 140° C. oven for an initial period of approximately 14 hours. A subsequent infrared spectra was taken after the initial 14 hour period to determine if all of the anhydride has been reacted. If anhydride is detected, the reactor should be placed in the 140° C. oven until subsequent infrared spectra do not detect the presence of anhydride, which indicates that the reaction is complete. If necessary, proplyeneglycol monomethylether acetate (PM acetate) may be added after the reaction is complete to reduce the viscosity of the final product for easy handling.

EXAMPLE 4

This example illustrates the preparation of an anhydride adduct from the reaction of 2-vinyl-5-ethyl-5-hydroxymethyl-1,3-dioxane (VDO-6) and methylhexahydrophthalic anhydride (MHHPA). A reactor was charged with 10.75 g of VDO-6, 10.25 g of MHHPA, and 9.00 g of PM Acetate. After an infrared spectra of the reactor contents were taken, the reactor was placed in a 140° C. oven for an initial period of approximately 60 hours. A subsequent infrared spectra was taken after the initial 60 hour period to determine if all of the anhydride has been reacted. If anhydride is detected, the reactor should be placed in the 140° C. oven until subsequent infrared spectra do not detect the presence of anhydride, which indicates that the reaction is complete.

EXAMPLE 5

This example illustrates the preparation of an monoepoxyester adduct from the reaction of the anhydride adduct with a monoepoxyester. A reactor was charged with a first feed stream comprising 549.61 g of 2-vinyl-5-ethyl-5-hydroxymethyl-1,3-dioxane (VDO-6), 536.83 g of methyl-hexahydrophthalic anhydride (MHHPA), and 68.06 g of butyl acetate, and a nitrogen purge was placed on the reactor. The reactor contents were heated to 150° over approximately a twenty minute period. The heat source was removed and the exothermic reaction increased the temperature of the reactor contents to approximately 190° C. over the next 30 minutes. The reactor was charged with a second feed stream comprising 811.64 g of Cardura E-10 over a period of approximately 25 minutes. A third feed steam comprising 1.90 g of dibutyl tin dilaurate (DBDTA) and 31.95 g butyl acetate was charged to the reactor, and the reactor was heated to a reflux temperature of approximately 175° C. and held for 3 hours.

The best mode presently contemplated for carrying out the invention is represented by the disclosure and claims herein, it being understood that selection of the best mode will depend on a variety of factors. Those skilled in the art will no doubt be able to compose numerous variations on the themes disclosed, such as changing the amounts of ingredients insignificantly from those shown, adding innocuous or supplementary substances, or substituting equivalent components for those shown. Such variations are considered to be within the inventive concept, as defined in the following claims.

We claim:

1. A curable coating composition comprising about 5 to 75% by weight of a liquid organic carrier and about 25 to 95% by weight, based on the weight of the composition, of a binder wherein the binder further comprises:

a) from about 10 to 45%, based on the weight of the binder, of the adduct of a vinyldioxo compound with a cyclic compound, the adduct being represented by the formula

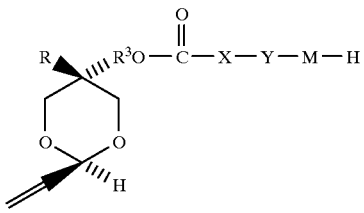

wherein X is selected from the group consisting of linear alkyls having 1 to 12 carbon atoms, branched alkyls having 3 to 12 carbon atoms, and cyclic alkyls having 3 to 12 carbon atoms; Y is selected from the group consisting of $CH_2$, $CHR'$, $CR'R''$, and carbonyls; M is oxygen; and each R, R', R", and $R^3$ is independently selected from the group consisting of linear alkyls having 1 to 12 carbon atoms, branched alkyls having 3 to 12 carbon atoms, and cyclic alkyls having 3 to 12 carbon atoms;

b) from about 15 to 40%, based on the weight of the binder, of other film forming polymers;

c) from about 10 to 40%, based on the weight of the binder, of a crosslinking agent; and d) from about 0 to 15%, based on the weight of the binder, of other additives.

2. The curable coating composition of claim 1 wherein the adduct of claim 1 is replaced by the an adduct of a vinyldioxo compound and a cyclic compound which is a cyclic anhydride, the adduct being represented by the formula

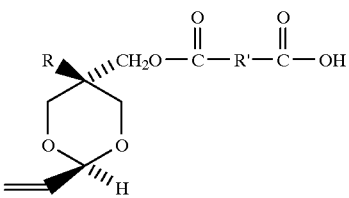

wherein each R and R' is independently selected from the group consisting of linear alkyls having 1 to 12 carbon atoms; branched alkyls having 3 to 12 carbon atoms; and cyclic alkyls having 3 to 12 carbon atoms.

3. The curable coating composition of claim 1 wherein the adduct of claim 1 is replaced by an adduct of a vinyldioxo compound and a lactone; the adduct being represented by the generic formula

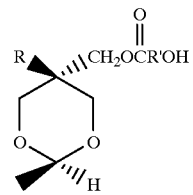

wherein each R and R' is independently selected from the group consisting of linear alkyls having 1 to 12 carbon atoms; branched alkyls having 3 to 12 carbon atoms; and cyclic alkyls having 3 to 12 carbon atoms.

4. The curable coating composition of claim 2 wherein the adduct of claim 2 is replaced by the adduct which is further reacted with an epoxyester, the adduct being represented by the formula:

a)

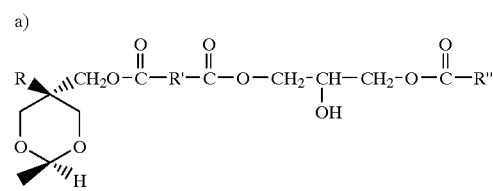

b)

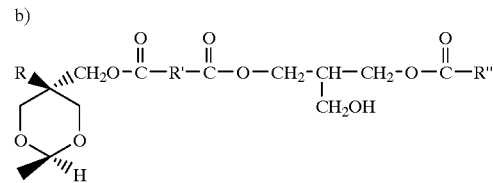

and c) mixtures of a) and b);

wherein each R, R', and R" is independently selected from the group consisting of linear alkyls having 1 to 12 carbon atoms; branched alkyls having 3 to 12 carbon atoms; and cyclic alkyls having 3 to 12 carbon atoms.

5. A curable coating composition comprising about 5 to 75% by weight of a liquid organic carrier and about 25 to 95% by weight, based on the weight of the composition, of a binder wherein the binder further comprises:

a) from about 10 to 45%, based on the weight of the binder, of the adduct of a vinyldioxo compound with a cyclic compound, the adduct being represented by the formula and a cyclic compound; wherein said cyclic compound consists of a lactam, the adduct being represented by the formula

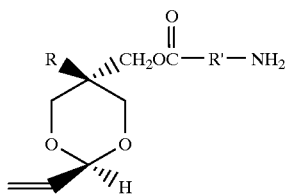

wherein each R and R' is independently selected from the group consisting of linear alkyls having 1 to 12 carbon atoms; branched alkyls having 3 to 12 carbon atoms; and cyclic alkyls having 3 to 12 carbon atoms;

b) from about 15 to 40%, based on the weight of the binder, of other film forming polymers;

c) from about 10 to 40%, based on the weight of the binder, of a crosslinking agent; and d) from about 0 to 15%, based on the weight of the binder, of other additives.

* * * * *